United States Patent [19]

Kamegai et al.

[11] Patent Number: 5,062,989

[45] Date of Patent: Nov. 5, 1991

[54] DETERGENT COMPOSITION

[75] Inventors: Jun Kamegai, Ichikawa; Masatoshi Arisawa, Matsudo, both of Japan

[73] Assignee: Kao Corporation, Tokyo, Japan

[21] Appl. No.: 295,389

[22] Filed: Jan. 10, 1989

[30] Foreign Application Priority Data

Jan. 12, 1988 [JP] Japan .................................. 63-4420

[51] Int. Cl.$^5$ .......................... C11D 7/00; C11D 3/04
[52] U.S. Cl. ................ 252/174.17; 252/135; 252/DIG. 5; 252/DIG. 13
[58] Field of Search ............ 252/174.17, 135, DIG. 5, 252/DIG. 13

[56] References Cited

U.S. PATENT DOCUMENTS

| | | | |
|---|---|---|---|
| 3,892,681 | 7/1975 | Edwards et al. | 252/174.17 |
| 4,396,520 | 8/1983 | Payne et al. | 252/174.17 |
| 4,483,780 | 11/1984 | Llenado | 252/174.17 |
| 4,536,317 | 8/1985 | Llenado | 252/174.17 |
| 4,565,647 | 1/1986 | Llenado | 252/DIG. 13 |
| 4,732,696 | 3/1988 | Urfer | 252/135 |
| 4,758,376 | 7/1988 | Hirota et al. | 252/DIG. 13 |
| 4,780,250 | 10/1988 | Urfer et al. | 252/174.17 |
| 4,804,497 | 2/1989 | Urfer et al. | 252/174.17 |

FOREIGN PATENT DOCUMENTS

| | | |
|---|---|---|
| 919424 | 1/1973 | Canada . |
| 0070076 | 1/1983 | European Pat. Off. . |
| 0075995 | 4/1983 | European Pat. Off. . |
| 0092877 | 11/1983 | European Pat. Off. . |
| 0136844 | 4/1985 | European Pat. Off. . |
| 2185991 | 8/1987 | United Kingdom . |
| 8602943 | 5/1986 | World Int. Prop. O. . |

Primary Examiner—Paul Lieberman
Assistant Examiner—Williams S. Parks

Attorney, Agent, or Firm—Oblon, Spivak, McClelland, Maier & Neustadt

[57] ABSTRACT

A detergent composition comprising a phosphate-type surface active agent and an alkyl saccharide-type surface active agent is described. The phosphate-type surface active agent which can be used have the following formula (I) or (II), and the alkyl saccharide-type surface active agent have the following formula (III):

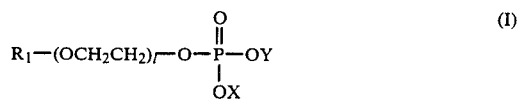

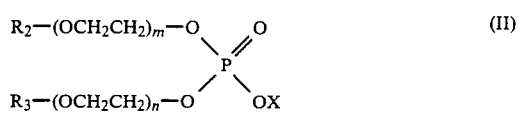

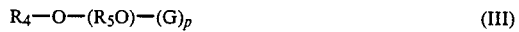

wherein $R_1$, $R_2$, $R_3$, and $R_4$ represent a linear or branched alkyl, alkenyl group, or alkyl phenyl groups of a $C_{8-18}$ carbon atom content, X and Y represent a hydrogen atom, an alkali metal, an ammonium, or an alkanol amine having a hydroxyl alkyl group of a a $C_{2-3}$ carbon atom content, $R_5$ represents an alklene group of a $C_{2-4}$ carbon atom content, G represents a reduced sugar of a $C_{5-6}$ carbon atom content, and l, m, n, and p denote a value of 0 to 10. The detergent composition exhibits exceptionaly good detergent capability and foaming capability. In addition, it imparts less irritation to the hair and skin, less creaking feeling to the hair, and superior smooth and moistened feeling to the skin.

6 Claims, No Drawings

DETERGENT COMPOSITION

BACKGROUND OF THE INVENTION

1. Field of the Invention

This invention relates to a detergent composition, and, more particularly, to a detergent composition comprising a phosphate-type surface active agent and an alkyl saccharide-type surface active agent. The detergent composition possesses a high foaming capability and is slightly irritative.

2. Description of the Background

Phosphate-type surface active agents impart less irritation to the skin than soaps, alkyl sulfates, or alkylether sulfate, and hence have widely been applied as body washing soaps and shampoos (Japanese Patent Publication No. 9033/1980 and Japanese Patent Publication No. 47959/1982).

Phosphate-type surface active agents, however, readily react to combine with calcium in water producing deposits of calcium phosphate, which impairs detergent capability, foaming capability, and the feeling upon use. This brings about the problem of an increased dry feeling to the hair and a powdery feeling to the skin.

In order to solve this problem the addition of a calcium ion chelating agent such as ethylenediamine tetraacetic acid (U.S. Pat. No. 4,303,556) and the addition of an amine oxide or betaine-type surface active agent as an insoluble surfactant-dispersing agent (Japanese Patent Laid-open No. 138594/1987, Japanese Patent Laid-open No. 74196/1984, and Japanese Patent Laid-open No. 103598/1983) have been proposed.

On the other hand, alkyl saccharides have been known as imparting only low irritation to the skin. Known alkyl saccharides include β-alkyl saccharide such as octyl- or nonylglucoxide, decyl-, dodecyl-, or tridecylmaltoside, etc., and alkyl saccharides synthesized from a reduced sugar such as glucose, galactose, maltose, or the like and a higher alcohol (U.S. Pat. No. 3,219,656, U.S. Pat. No. 3,598,865, and U.S. Pat. No. 3,839,318).

These surface active agents, however, if used independently, pose problems of insufficient foaming capability and poor detergent capability. In addition, they impart dry, uncomfortable feeling when used as a detergent for washing hair or skin. For these reasons, use of these compounds as a detergent in combination with an anionic surface active agent (Japanese Patent Laid-open No. 130210/1984) or a nonionic surface active agent (Japanese Patent Laid-open No. 18594/1985) have been proposed.

Use of a phosphate-type surface active agent in combination with a chelating agent, however, does not bring about satisfactory effect. If used at a high concentration, the chelating agent increases irritativeness imparted by the detergent composition. Addition of a dispersing agent also entails problems of poor foaming capability, greater irritativeness, and insufficient detergent capability.

Also, no detergent compositions, providing low irritativeness, excellent detergent capability, and an acceptable feeling on use, have been developed through the use of alkyl saccharide-type surface active agents.

In view of this situation, the present inventors have undertaken extensive studies to obtain a detergent composition which is free from the above problems. As a result, the inventors have found the use of a specific of phosphate-type surface active agent in conjunction with a specific alkyl saccharide-type surface active agent causes insoluble phosphate salts to be solubilized or dispersed, increases detergent capability of the composition, enhances foaming capability, and decreases irritation to the hair or skin. These findings have led to the completion of this invention.

SUMMARY OF THE INVENTION

Accordingly, an object of the present invention is to provide a detergent composition comprising:

(A) a phosphate-type surface active agent represented by the following formula (I):

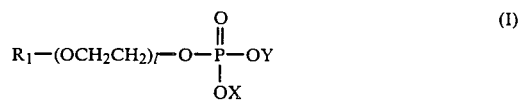

wherein $R_1$ represents a linear or branched alkyl group of a $C_{8-18}$ carbon atom content, a linear or branched alkenyl group of a $C_{8-18}$ carbon atom content, or an alkyl phenyl group of a $C_{8-18}$ carbon atom content, with the alkyl group being either linear or branched, X and Y independently represent a hydrogen atom, an alkali metal, an ammonium, or an alkanol amine having a hydroxyl alkyl group of a a $C_{2-3}$ carbon atom content, and 1 denotes a value of 0 to 10, or a phosphate-type surface active agent represented by the following formula (II):

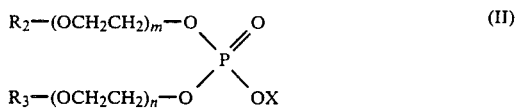

$R_2$ and $R_3$ independently represent a linear or branched alkyl group of a $C_{8-18}$ carbon atom content, a linear or branched alkenyl group of a $C_{8-18}$ carbon atom content, or an alkyl phenyl group of a $C_{8-18}$ carbon atom content, with the alkyl group being either linear or branched, X has the same meaning as defined in formula (I), and m and n independently denote a value of 0 to 10, or a mixture thereof, and (B) an alkyl saccharide-type surface active agent represented by the following formula (III):

wherein $R_4$ represents a linear or branched alkyl group of a $C_{8-18}$ carbon atom content, a linear or branched alkenyl group of a $C_{8-18}$ carbon atom content, or an alkyl phenyl group of a $C_{8-18}$ carbon atom content, with the alkyl group being either linear or branched, $R_5$ represents an alkylene group of a $C_{2-4}$ carbon atom content, G represents a reduced sugar of a $C_{5-6}$ carbon atom content, and p denotes a value of 1 to 10.

Other objects, features and advantages of the invention will hereinafter become more readily apparent from the following description.

DETAILED DESCRIPTION OF THE INVENTION AND PREFERRED EMBODIMENTS

Desirable phosphate-type surface active agents used as the (A) component in this invention are those having 0 to 3 mole of the added ethylene oxide. Especially desirable phosphate-type surface active agents are those having no ethylene oxide added thereto and having an alkyl group with a $C_{12-14}$ carbon atom content. Specific examples of preferable (A) components are sodium mono- or dilauryl phosphate, diethanolamine mono- or dilauryl phosphate, triethanolamine mono- or dilauryl phosphate, sodium mono- or dimyristyl phosphate, potassium mono- or dimyristyl phosphate, diethanolamine mono- or dimyristyl phosphate, triethanolamine mono- or dimyristyl phosphate, and the like. As the (A) component, use of compounds of formulae (I) and (II) at a ratio of 10/0-5/5 is preferable, with especially preferable range being 10/0-7/3.

It is desirable that the (A) component be formulated into the detergent composition of this invention in an amount of 5 to 50% by weight. When the composition is a shampoo the amount of 5 to 20% by weight is preferable. When it is a composition for use with the skin the amount of 5 to 40% by weight is preferable.

As an alkyl saccharide-type surface active agent, which is the (B) component of this invention, those having an alkyl group for $R_4$ with 8 to 18, particularly 10 to 14 (lauryl group, myristyl group, etc.), carbon atoms are preferable. The basic unit for the saccharide portion [G in formula (III)], which is the hydrophilic group of the alkyl saccharide-type surface active agent, is a reducing sugar having a $C_{5-6}$ carbon atom content. Glucose, galactose, and fructose are named as examples of desirable reducing sugars. The degree of the polymerization (S) of saccharide, i.e., the value of p in formula (III), is 1 to 10. In particular, use of reducing sugars containing 80% or more of those having the degree of the polymerization (S) of 1 to 4 is desirable. The compounds of formula (III) having a lower degree of the polymerization (S), e.g. 1 to 1.4, are desirable. When the property of the compounds of formula (III) due to the group $R_4$ is taken into account, the value for the polymerization (S) of 1 to 1.4 is desirable for the $R_4$ group with $C_{8-11}$, and (S) of 1.5 to 4.0 is desirable for the $R_4$ group $C_{12-14}$. The mean values for (S) were determined by proton-NMR method.

It is desirable that the (B) component be formulated into the detergent composition of this invention in an amount of 0.1 to 40% by weight. When the composition is a shampoo the amount of 2 to 10% by weight is preferable. When it is a composition for use with the skin the amount of to 20% by weight is preferable. The amount of 10 to 35% by weight is particularly preferable for the composition used as a detergent for washing fine fabric clothing.

To the detergent composition of this invention, beside the essential components (A) and (B) various components conventionally used for detergent compositions can be formulated as appropriate to the extent that the effect of this invention is not impaired. Examples of such other components include humectants such as propylene glycol, sorbitol, glycerol, and the like; viscosity adjusting agents such as carboxyvinyl polymers, methyl cellulose, ethanol, polyoxyethyleneglycol distearate, and the like, pearling agents, perfumes, coloring agents, UV absorbers, antioxidants bactericides, antiseptics, antiphlogistics, and the like.

The detergent composition of this invention can be prepared in a form conventionally employed for detergent composition. The proportion of the surface active agents, i.e. the proportion of components (A) plus (B), in the composition is desirably 30% by weight or more in the case of a solid-type composition, 20% by weight or more in the case of the composition in a form of paste, and 10% by weight or more in the case of a liquid detergent composition.

Since in the detergent composition of this invention calcium salts of surface active agent produced from phosphate-type surface active agents and calcium contained in water can be effectively dispersed and solubilized through the action of an alkyl saccharide-type surface active agent, the composition exhibits exceptionally good detergent capability and foaming capability. In addition, it imparts less irritation to the hair and skin, less creaking feeling to the hair, and superior smooth and moistened feeling to the skin.

Other features of the invention will become apparent in the course of the following description of the exemplary embodiments which are given for illustration of the invention and are not intended to be limiting thereof.

EXAMPLES

EXAMPLE 1

Detergent compositions listed in Table 1 were prepared. The detergency and the foaming capability of each composition were measured using the Terg-O-Tometer method and a reverse stirring method, respectively. In addition, the feeling to touch imparted to hands during washing using the composition was evaluated by 10 expert panelists according to the following standard.

O: Feeling was good
X: Feeling was bad
The results are shown in Table 1.

TABLE 1

|  | Invention Composition | | | Comparative Composition | | | |
| --- | --- | --- | --- | --- | --- | --- | --- |
|  | 1 | 2 | 3 | 1 | 2 | 3 | 4 |
| Lauryl phosphate ditriethanolamine | 10 | 10 | 10 | 15 | 10 | 10 |  |
| Alkyl saccharide[1] $C_{12.13}$—O—$(G)_{2.5}$ | 5 |  |  |  |  |  | 15 |
| Dodecyl maltoside |  | 5 |  |  |  |  |  |
| Octyl glucoside |  |  | 5 |  |  |  |  |
| Polyoxyethylene (25) dodecylether |  |  |  |  | 5 |  |  |
| Cocodiethanolamide |  |  |  |  |  | 5 |  |
| Ion-exchanged water | 85 | 85 | 85 | 85 | 85 | 85 | 85 |
| Detergency[2] (%) | 65.8 | 73.2 | 65.1 | 14.7 | 25.1 | 30.5 | 40.0 |
| Foaming ability[2] (ml) | 70.3 | 91.2 | 60.3 | 25.0 | 14.0 | 31.0 | 100 |

TABLE 1-continued

|  | Invention Composition | | | Comparative Composition | | | |
| --- | --- | --- | --- | --- | --- | --- | --- |
|  | 1 | 2 | 3 | 1 | 2 | 3 | 4 |
| Feeling during washing | ○ | ○ | ○ | X | X | X | X |

[1]$C_{12,13}$: A mixture of dodecyl group and tridecyl group, with an average carbon atom content of 12.5; G: glucose

[2]The characteristics were measured using a 1% by weight solution of the detergent in water with a 15° hardness (German hardness).

EXAMPLE 2

SHAMPOO COMPOSITION

Formulation:

| (1) Lauryl phosphate sesquitriethanolamine | 20 wt % |
| --- | --- |
| (2) Alkyl saccharide $(C_{12}-O-(G)_{1.45})^3$ | 5 wt % |
| (3) Cocodiethanolamide | 2 wt % |
| (4) Cocoimidazolinium betaine | 4 wt % |
| (5) No. 4 Yellow | Small amount |
| (6) Perfume | Small amount |
| (7) Ion-exchanged water | Balance |

[3]$C_{12}$: lauryl group; G: glucose

Preparation:

Into ion-exchanged water heated to 50° C., component (1) and then components (2), (3), and (4) were dissolved. After cooling the solution, components (5) and (6) were added to it.

This shampoo composition containing a phosphate-type surface active agent and an alkyl saccharide-type surface active agent was free from dry feeling, was easily and swiftly rinsed, and produced abundant foam.

EXAMPLE 3

SHAMPOO COMPOSITION

Formulation:

| (1) Lauryl phosphate sesquitriethanolamine | 10 wt % |
| --- | --- |
| (2) Alkyl saccharide $(C_{12}-O-(G)_{2.5})^4$ | 15 wt % |
| (3) Cocoimidazolinium betaine | 2 wt % |
| (4) Cationic polymer[5] | 0.5 wt % |
| (5) Polyoxyethylene (EO 100) distearic acid ester[6] | 2 wt % |
| (6) Ethylene glycol distearate[7] | 2 wt % |
| (7) No. 4 Yellow | Small amount |
| (6) Perfume | Small amount |
| (7) Ion-exchanged water | Balance |

[4]$C_{12}$: lauryl group; G: glucose
[5]Polymer JR-400, manufactured by Union Carbide Corp.
[6]Emanon 3299R, manufactured by Kao Corp.
[7]Emanon 3201M, manufactured by Kao Corp.

Preparation:

Component (1) was dispersed into component (4) under heating at 80° C. To this dispersion components (2), (3), (5) and (6) were added and the mixture was stirred. After cooling the mixture, components (7) and (8) were added to it.

This shampoo composition containing a phosphate-type surface active agent and an alkyl saccharide-type surface active agent was free from dry feeling, provided smooth and moistened feeling, and produced abundant foam.

EXAMPLE 4

BODY COMPOSITION

Formulation:

| (1) Lauryl phosphate ditriethanolamine | 20 wt % |
| --- | --- |
| (2) Alkyl saccharide $(C_{12}-O-(G)_2)^8$ | 15 wt % |
| (3) lauric acid | 4 wt % |
| (4) denatured alcohol | 3 wt % |
| (5) No. 4 Yellow | Small amount |
| (6) Perfume | Small amount |
| (7) Ion-exchanged water | Balance |

[8]$C_{12}$: cocoyl group; G: galactose

Preparation:

To ion-exchanged water heated to 70° C., components (1), (2), and (3) were added to dissolve. After cooling the solution to 50° C., component (4) were added. The mixture was further cooled to 40° C., and components (5) and (6) were added to it.

This body shampoo composition containing a phosphate-type surface active agent and an alkyl saccharide-type surface active agent produced abundant foam, was easily and swiftly rinsed, and provided smooth feeling to the skin after drying.

EXAMPLE 5

FACE WASHING FOAM

Formulation:

| (1) Lauryl phosphate ditriethanolamine | 5 wt % |
| --- | --- |
| (2) Myristyl phosphate ditriethanolamine | 10 wt % |
| (3) Alkyl saccharide $(C_{12}-O-(G)_{2.5})^9$ | 25 wt % |
| (4) Lauric acid | 4 wt % |
| (5) Ethylene glycol distearate | 4 wt % |
| (6) Hydroxyethyl cellulose | 0.5 wt % |
| (7) No. 4 Yellow | Small amount |
| (8) Perfume | Small amount |
| (9) Ion-exchanged water | Balance |

[9]$C_{12}$: cocoyl group; G: glucose
[10]Emanon 3201M, manufactured by Kao Corp.

Preparation:

Into ion-exchanged water heated to 50 C, component (1) was dissolved and component 6]was added to disperse. Then, to the mixture components (2), (3), and (4) were further added to dissolve. Upon confirming the dissolution of components (2), 3), and (4), component (5) was added to dissolve. After cooling the solution, components (7) and (8) were added to it.

This face washing foam composition containing a phosphate-type surface active agent and an alkyl saccharide-type surface active agent produced abundant foam, was easily and swiftly rinsed, and provided smooth feeling to the skin after drying.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent:

1. A shampoo, skin cleanser or fine fabric detergent composition consisting essentially of:

(A) 5-50 wt. % of a phosphate-type surface active agent represented by the following formula (I):

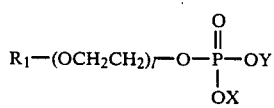  (I)

wherein $R_1$ represents a linear or branched alkyl group of a $C_{8-18}$ carbon atom content, a linear or branched alkenyl group of a $C_{8-18}$ carbon atom content, or an alkyl phenyl group of a $C_{8-18}$ carbon atom content, with the alkyl group being either linear or branched, X and Y independently represent a hydrogen atom, an alkali metal, an ammonium, or an alkanol amine having a hydroxyl alkyl group of a $C_{2-3}$ carbon atom content, and l denotes a value of 0 to 10, or a phosphate-type surface active agent represented by the following formula (II):

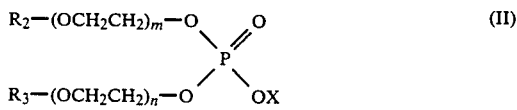  (II)

$R_2$ and $R_3$ independently represent a linear or branched alkyl group of a $C_{8-18}$ carbon atom content, a linear or branched alkenyl group of a $C_{8-18}$ carbon atom content, or an alkyl phenyl group of a $C_{8-18}$ carbon atoms content, with the alkyl group being either linear or branched, X has the same meaning a defined in formula (I), and m and n independently denote a value of 0 to 10, or a mixture thereof, and (B) 0.1-40 wt. % of an alkyl saccharide-type surface active agent represented by the following formula (III):

  (III)

wherein $R_4$ represents a linear or branched alkyl group of a $C_{8-18}$ carbon atom content, a linear or branched alkenyl group of a $C_{8-18}$ carbon atom content, or an alkyl phenyl group of a $C_{8-18}$ carbon atom content, with the alkyl group being either linear or branched, $R_5$ represents an alkylene group of a $C_{2-4}$ carbon atom content, G represents a reduced sugar of a $C_{5-6}$ carbon atom content, and p denotes a value of 1 to 10, said (A) and (B) constituting at least about 80 wt. % of the surfactants present in said detergent composition.

2. The detergent composition according to claim 1 in the form of a shampoo, wherein phosphate-type surface active agent (A) is present in an amount of 5-20% by weight and the alkyl saccharide-type surface active agent (B) is present in an amount of 2-10% by weight.

3. The detergent composition according to claim 1 for skin use, wherein the phosphate-type surface active agent (A) is present in an amount of 5-40% by weight and the alkyl saccharide-type surface active agent (B) is present in an amount of 5-20% by weight.

4. The detergent composition according to claim 1 for washing fine fabric clothing, wherein the alkyl saccharide-type surface active agent (B) is present in an amount of 10-35% by weight.

5. The detergent composition according to claim 1, wherein the ratio of phosphate-type surface active agents I/II equals 10/0-5/5.

6. The detergent composition according to claim 1, wherein the ratio of phosphate-type surface active agents I/II equals 10/0-7/3.

* * * * *